United States Patent [19]

Chapman et al.

[11] Patent Number: 5,763,683

[45] Date of Patent: Jun. 9, 1998

[54] 2-METHYLBUTOXY ETHOXYETHANOL

[75] Inventors: Richard George Chapman, Weybridge; Nicholas John Hazel, Beverley; Nevin John Stewart, Guildford; Stephen Paul Goodwin, London; Andrew Richard Lucy, Hotham, all of England

[73] Assignee: BP Chemicals Limited, London, England

[21] Appl. No.: 495,523

[22] PCT Filed: Dec. 13, 1994

[86] PCT No.: PCT/GB94/02721

§ 371 Date: Sep. 19, 1995

§ 102(e) Date: Sep. 19, 1995

[87] PCT Pub. No.: WO95/17367

PCT Pub. Date: Jun. 29, 1995

[30] Foreign Application Priority Data

Dec. 23, 1993 [GB] United Kingdom ............... 9326328

[51] Int. Cl.$^6$ ............................. C07C 41/00; C07C 43/00
[52] U.S. Cl. ............................................ 568/675; 568/672
[58] Field of Search ............................... 568/672, 675

[56] References Cited

U.S. PATENT DOCUMENTS

| 3,656,881 | 4/1972 | Hemwall | 8/94.23 |
| 4,187,384 | 2/1980 | Platz et al. | 568/618 |
| 4,898,992 | 2/1990 | Stankowiak et al. | 568/618 |

Primary Examiner—Marianne M. Cintins
Assistant Examiner—Dwayne C. Jones
Attorney, Agent, or Firm—Fay, Sharpe, Beall, Fagan, Minnich & McKee

[57] ABSTRACT

A novel 2-Methylbutoxy ethoxyethanol and a method for the preparation thereof. The use of the novel 2-Methylbutoxy ethoxyethanol as a solvent or a coalescing aid in aqueous formulations used as coatings and paints, a cleaning solvent for electronic components, a domestic and industrial hard surface cleaner, a component of oil well drilling muds, a fuel additive, and a solvent for liquid detergents.

9 Claims, No Drawings

2-METHYLBUTOXY ETHOXYETHANOL

This application is a 371 of PCT/GB94/02721 filed on Dec. 13, 1994.

This invention relates to a novel ether 2-methylbutoxy ethoxy ethanol, a process for the preparation thereof and the use thereof as a cosolvent in aqueous resin formulations.

Monoethers of diethyleneglycol in general are well known in the art. However, the specific monoether of diethylene glycol of the present invention is unique especially in its properties in aqueous based resin systems.

Accordingly, the present invention is 2-methylbutoxy ethoxyethanol represented by the formula:

$CH_3\text{-}CH_2\text{-}CH(CH_3)\text{-}CH_2\text{-}O\text{-}CH_2\text{-}CH_2\text{-}O\text{-}CH_2\text{-}CH_2\text{-}OH$ 2-Methylbutoxy ethoxy ethanol (hereafter "2-MBDGE") is an ether which can be synthesised by the dropwise addition of 1-chloro-2-methylbutane to a stirred mixture of a molar excess of diethylene glycol and an equimolar amount of an aqueous alkali, eg sodium hydroxide, at elevated temperature under cover of a gas inert under the reaction conditions eg nitrogen. The reaction mixture is maintained at this elevated temperature over a period and then cooled. The cold reaction mixture is then extracted with a suitable solvent such as eg dichloromethane. The resultant extract in the solvent is washed repeatedly with eg water, dried and subjected to fractional distillation, suitably under a high vacuum when 2-MBDGE is collected as a colourless mobile liquid emerging at eg 82° C./1 mm Hg. 2-MBDGE has a boiling point of about 240° C. and was characterised by $^{13}C$ NMR spectroscopy.

2-MBDGE may also be prepared by the reaction of 2-methyl butanol with ethylene oxide at elevated temperature and pressure and in the presence of a catalyst, preferably a base catalyst such as potassium acetate.

2-MBDGE, which is also called 2-methyl butyldiglycol ether, is unique in that it is capable of exhibiting unexpected behaviour as a cosolvent in aqueous resin formulations used eg in coatings and in paints. It is well known that some resins used for water-based coatings are largely incompatible with water, and that the compatibility with water can be improved by the addition of an organic solvent known as a "coupling solvent". The nature of the coupling solvent used can affect the performance of the formulated coating in several ways.

The "coupling power" of the solvent relates to how good the solvent is at increasing the solubility of the resin in water. A solvent good in this respect can, among other benefits, increase the range of humidity and/or temperature at which the coating may be successfully applied. A simple measure of the "coupling power" of the solvent may be obtained by adding water to a 30:70 by weight mixture of coupling solvent and n-heptane at room temperature, where the n-heptane acts as a model for an oleophilic resin. At some point as water addition is increased, the mixture moves from a single, homogeneous phase to a mixture of two phases. The amount of water added before the appearance of the second phase is an indication of the coupling power of the solvent. The objective is to maximise the amount of water that can be added to the coupling solvent before the second phase appears.

The rheology of a coating formulation is partly determined by the composition and phase behaviour of the water/resin/coupling solvent ternary mixture. A good coupling solvent can influence the rheology such that, eg, the process of formulating the coating is simplified by minimising viscosity variations when a solution of the resin in the coupling solvent is diluted with water. Effectively, it is believed that the coupling solvent associates preferentially with the organic phase rather than the aqueous phase. A good solvent can also improve the performance of the coating when applied to a substrate by, eg, reducing sagging and curtaining effects. Desirable rheological behaviour is related to the composition of the ternary mixture such that, when two liquid phases coexist, one of the phases should be very largely comprised of water. This behaviour is easily determined using a model system with n-heptane and carrying out the test to measure coupling power as described above. When just sufficient water is added so that a second phase begins to appear as signified by the formation of small droplets, these droplets are largely comprised of water whereas the larger organic phase comprises mainly n-heptane and the coupling solvent (shown as notation (d) in the Table below); the behaviour would be considered undesirable if two phases are formed which are comparable in volume and one of the phases is largely comprised of n-heptane (shown as notation (nd) in the Table below).

A coupling solvent for use in coatings should have a higher boiling point than water such that the coupling solvent allows a film of the coating applied on a substrate to dry as a continuous phase, ie the water evaporates faster than the solvent.

The surprising aspect of the invention may be seen in the Table below by comparing the performance in respect of coupling power and phase behaviour of 2-MBDGE with that of other high-boiling coupling solvents, for example 2-(2-butoxyethoxy)ethanol (hereafter "BDGE") and hexyl glycol ether (hereafter "HGE"), which boil at 231° C. and 208° C. respectively. The data in the Table show that, for coatings applications where high boiling solvents may be used, 2-MBDGE shows the desired phase behaviour and a significant improvement in respect of coupling power when compared with the conventional coupling solvents used hitherto.

In addition to its use as a coupling solvent in aqueous based resin formulations, 2-MBDGE of the present invention can be used as a coalescing aid in paints, as a cleaning solvent for eg electronic components in order to free them from residues such as fluxes and resins, in domestic and industrial hard surface cleaning agents, in oil well drilling muds, as a fuel additive and as a solvent for liquid detergents.

The novel ether of the present invention, its synthesis and use is further illustrated with reference to the following Examples:

EXAMPLES

1. Synthesis of 2-MBDGE:

To a 5-liter three-necked round-bottomed flask equipped with a mechanical stirrer, thermometer, condenser and addition funnel was added diethylene glycol (3040 g, 28.6 moles). This was heated with stirring under nitrogen to 60° C. and a 50% aqueous solution of sodium hydroxide (225 g, 5.6 moles) added. The mixture was then heated to 93° C. and 1-chloro-2-methylbutane (594 g, 5.6 moles, containing 3-4% 1-chloro-3-methylbutane) was added dropwise over 3 hrs and heating and stirring continued for a further 60 hrs. The mixture was then allowed to cool. From this mixture, a liquid layer was collected. The solid salts remaining as residue in the mixture after removal of the liquid layer were extracted with dichloromethane (2500 ml) and removed by filtration. The liquid layer and the dichloromethane extract were combined and distilled water (3000 ml) added thereto and then vigorously mixed. The resultant mixture was allowed to separate into two layers, namely an organic layer and an aqueous layer. The organic layer was collected and again washed twice more with water until no diethylene glycol could be detected in the organic layer by GLC. The washed organic layer was then dried by passage through a compacted pad of anhydrous sodium sulphate. Dichloromethane was removed from the dried organic layer by flash distillation followed by distillation through a 2.54 cm, 5-plate Oldershaw column under high vacuum. 2-MBDGE (378 g, 38% yield) was collected as a colourless mobile liquid boiling at 82° C./1 mm Hg. The structure of this product was confirmed by $^{13}$C NMR spectroscopy recorded at ambient temperature which also showed the presence of 3–4% of the isomeric 3-methylbutoxy ethoxy ethanol. The following shows the detailed $^{13}$C NMR spectral assignments referenced to CDCl$_3$ at 77.1 ppm:

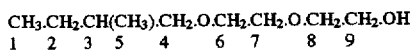

C1(10.7); C2(25.6); C3(34.2); C4(76.1); C5(15.9); C6(69.8); C7(69.8); C8(72.1); and C9(60.9) ppm.

The glycol ether had a boiling point of about 240° C. at ambient temperature and pressure.

2. Use of 2-MBDGE as a coupling solvent:

The performance of 2-MBDGE as a coupling solvent in aqueous n-heptane systems and its comparison with the performance of BDGE and HGE is tabulated below in Table 1. In the ternary phase behaviour, the mixture was derived by gradually adding water (% by weight) to a homogeneous solution of the glycol ether (30% by weight) and n-heptane (70% by weight):

TABLE 1

| COSOLVENT | TERNARY MIXTURE Amount of water added (% by wt) | |
|---|---|---|
| USED | Homogeneous | 2-Phases |
| BDGE * | 2 | 2.5 (nd) |
| HGE * | 1 | 1.5 (d) |
| 2-MBDGE | 5 | 6 (d) |

\* - comparative test not according to the invention
(nd) - substantial second phase having <50% wt/wt water
(d) - droplets of second phase having >50% wt/wt water 3. Use of 2-MBDGE as a coupling solvent with a resin:

The "coupling power" of 2-MBDGE in aqueous solutions of alkyd resin Croda N2/634 (ex Croda Resins, Belvedere, Kent, UK) and its comparison with the "coupling power" of HGE is tabulated below in Table 2. In the ternary phase behaviour, the mixture was derived by gradually adding water (% w/w) to a homogeneous solution of the glycol ether (40% w/w) and resin (60% w/w).

TABLE 2

| COSOLVENT | TERNARY MIXTURE Amount of water added (% by wt) | |
|---|---|---|
| USED | Homogeneous | 2-Phases |
| 2-MBDGE | 4.9 | 5.6 |
| HGE * | 3.7 | 4.2 |

\* - Comparative Test not according to the invention

We claim:

1. 2-methylbutoxy ethoxyethanol (2-MBDGE) represented by the formula:

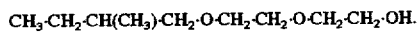

2. A method of making 2-methylbutoxy ethoxyethanol by reaction of 1-chloro-2-methylbutane with diethylene glycol said method comprising adding 1-chloro-2-methylbutane to a stirred mixture of a molar excess of diethylene glycol and an equimolar amount of an aqueous alkali at elevated temperature under cover of an inert gas under reaction conditions.

3. A method according to claim 2 wherein the aqueous alkali is aqueous sodium hydroxide solution.

4. A method according to claim 2 wherein the inert gas under reaction conditions is nitrogen.

5. A method according to claim 2 wherein the reaction mixture is maintained at an elevated temperature for a duration of about 63 hours, then cooled, the cold reaction mixture then extracted with a suitable solvent and the resultant solvent extract washed repeatedly with water, dried and subjected to fractional distillation, under a high vacuum to collect 2MBDGE as a colorless mobile liquid emerging at 82° C./1 mm Hg.

6. A method of making 2-methylbutoxy ethoxyethanol said method comprising reacting 2-methyl butanol with ethylene oxide at elevated temperature and pressure and in the presence of a catalyst.

7. A process according to claim 6 wherein the catalyst is a base catalyst.

8. A process according to claim 6 wherein the catalyst is potassium acetate.

9. A method of making a coupling solvent in aqueous based resin formulations; a coalescing aid in paints; a cleaning solvent for electric components in order to free said components from residues selected from fluxes and resins; a domestic and industrial hard surface cleaning agent; a component in oil well drilling muds; a fuel additive; and a solvent for liquid detergents comprising adding to said coalescing aid; said cleaning solvent, said cleaning agent; said component in oil well drilling muds; said fuel additive; and said solvent for liquid detergents, respectively, 2-methylbutoxy ethoxyethanol.

\* \* \* \* \*